United States Patent [19]

Tesi

[11] 3,977,237
[45] Aug. 31, 1976

[54] TONOMETER

[75] Inventor: Julius Michael Tesi, Buckeye Lake, Ohio

[73] Assignee: Julius M. Tesi

[22] Filed: July 14, 1975

[21] Appl. No.: 595,779

[52] U.S. Cl. .................................................. 73/80
[51] Int. Cl.² ........................................... A61B 3/16
[58] Field of Search ........................................ 73/80

[56] References Cited
UNITED STATES PATENTS

| | | | |
|---|---|---|---|
| 3,452,589 | 7/1969 | Hargens et al. | 73/80 |
| 3,531,984 | 10/1970 | Halberg | 73/80 |
| 3,597,964 | 8/1971 | Heine | 73/80 |
| 3,706,304 | 12/1972 | Sisler | 73/80 |
| 3,832,891 | 9/1974 | Stuckey | 73/80 |

FOREIGN PATENTS OR APPLICATIONS 116,633  10/1957  U.S.S.R. .............................. 73/80

Primary Examiner—James J. Gill
Assistant Examiner—Anthony V. Ciarlante
Attorney, Agent, or Firm—C. F. Schill; T. W. Winland; K. E. Shaweker

[57] ABSTRACT

A device for determining the level of intraocular pressure by applanation. The device includes a testing piston of precise weight which has one planar surface with an adjacent circular area of a predetermined radius. The weight of the piston flattens an area of the cornea being examined, and depending upon the intraocular pressure, the flattened area will be less than or greater than the circular area.

8 Claims, 9 Drawing Figures

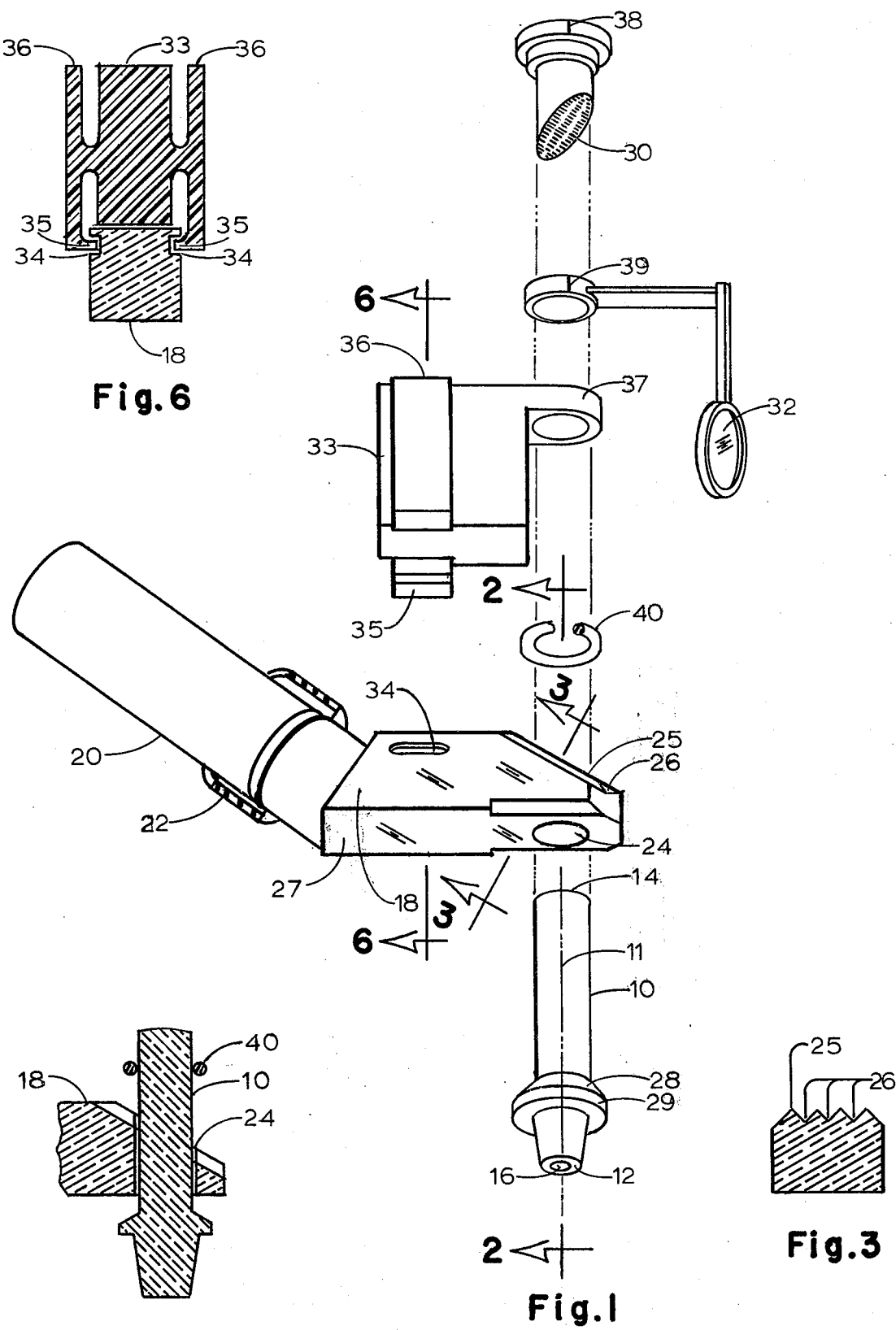

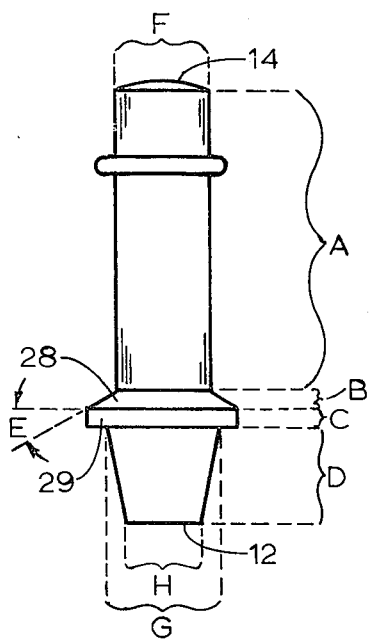
Fig.5
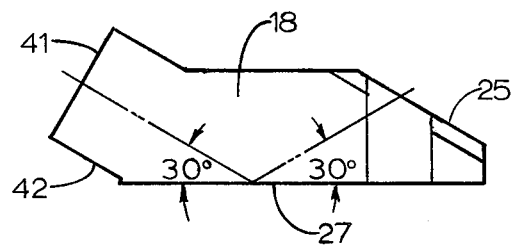
Fig.4
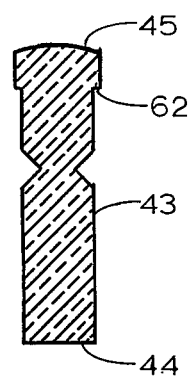
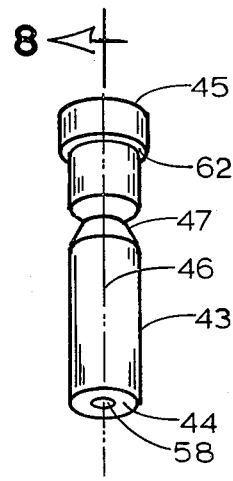
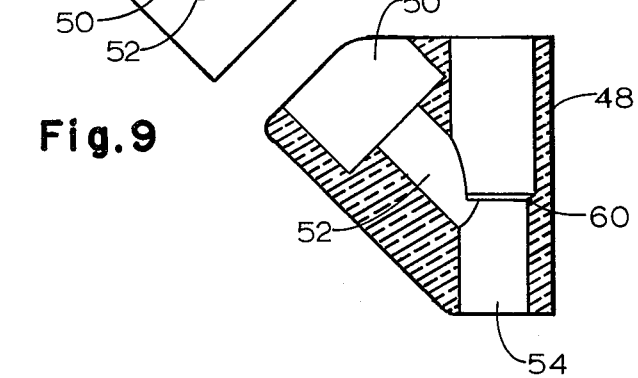
Fig.9  Fig.8
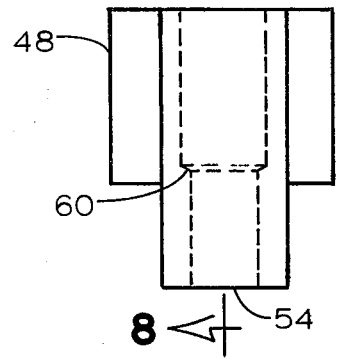
Fig.7

TONOMETER

BACKGROUND OF THE INVENTION

The present invention relates to a device for determining the level of the intraocular pressure of the human eye.

The intraocular pressure of a person's eye has been recognized as an important factor in the early detection of eye illnesses. Glaucoma, one such illness which occurs quite frequently in a large segment of the population, can be detected by an increase in intraocular pressure. By careful and routine screening, this condition may be recognized and treated before it progresses to theh point where blindness occurs. Since the most obvious early signal of glaucoma is an increase in pressure which is not easily detectable without proper screening, the ordinary person may not realize that there is a danger of this illness before other serious symptoms set in and additional damage is done to the eye. This damage can be prevented by early detection of the condition. Therefore, what is needed is a means for the physician in general practice to screen his patients on a routine basis for an increase in intraocular pressure above the accepted normal pressure which often indicates the initiation of glaucoma.

Unfortunately, the screening instruments presently available to the medical practitioner are of undue complexity, requiring continual recalibration or are so imprecise that they cannot provide a reliable check for the detection of imminent glaucoma.

Intraocular pressure is determined by two basic techniques: indentation or applanation tonometry. In indentation technique, a foot plate with a weight-loaded piston, whose specific weight can be varied, is lowered until it indents the cornea and the foot plate comes to rest on the cornea. The piston is forced upward by the resistance of the cornea being indented. As the piston is forced upward, this displacement is transmitted to a lever which actuates a pointer. The pointer then reads out on an attached scale, in mm of Hg, the resistance pressure, or distensibility of the eyeball, which is taken to be the intraocular pressure. A representative instrument of this type is the well known Schiotz tonometer.

The disadvantages of an instrument of this type are the many sources of error inherent in the instrument itself, i.e., it is affected by temperature, fulcrum friction, accumulation of debris on moving parts causing increased friction and must be frequently recalibrated. In addition, it is clumsy and difficult to use and inadvertent corneal abrasion may subsequently occur. Indentation produces relatively large volume displacement in the eye, which enhances the effects of varying scleral rigidity. All of the above tends to produce erroneous readings.

In applanation tonometry, the corneal curvature is flattened or applaned by a flat piston. The piston may be of known weight and the area of applanation determined by an indirect method or it may be of known surface area and the intraocular pressure necessary to applane that area is determined by calculating the force necessary to applane that area. Devices using pistons of known surface area are (1) Mackay-Marg which uses electronic means for readout, (2) the Goldmann slit lamp which uses an optical means for readout, and (3) the Tonour which uses a pumped pressure readout.

The well know Posner tonometer uses a piston of known weight which carries a stain on its contact surface. A print of the stain remaining on the piston after contact is transferred to a paper for measurement.

The disadvantages of the Posner instrument are the indirect readout of the area applaned by a known weight and the significant volume displacement caused by the large piston weight, which may produce erroneous readings. The transfer of area of stain remaining on the foot plate, after corneal contact, to a paper strip which is then measured on a scale is very difficult to use and produces many erroneous readings and thus, does not produce a reliable screening. The Mackay-Marg, Goldmann, and Tonour are complicated, expensive and difficult to use and thus, cannot be considered "screening" instruments.

An additional type of instrument described, for example, in U.S. Pat. No. 3,597,964, to Heine, dated Aug. 10, 1971, teaches the use of an applanation-type tonometer with a testing body of precisely determined weight to applane an area of the cornea. The area applaned can be compared to the diameter which would be applaned if the intraocular pressure were perfectly normal thereby indicating whether there is any possibility of glaucoma. This invention teaches the use of means for indicating the size of the applaned area which consists of an inner circle of a given radius and an outer surrounding area having a color different from the inner circle. These areas are formed either by inserting the testing body into a casing having the separate optical elements inside or by including a pair of transparent plane parallel oppositely inclined light-refracting plates in a hollow testing body. These plates are separated by a plane which contains the axis of the testing body and have a thickness and inclination to divide the viewed field into two halves. If the intraocular pressure deviates above or below a given value, these plates assume a shape which indicates the deviation from a predetermined intraocular pressure.

In addition, Heine teaches that the circular area applaned will equal the diameter of the circular area defined on the testing body when the intraocular pressure is 28.5 gm/cm$^2$ (or approximately 21 mm Hg).

The Heine patent teaches the use of a testing body in the form of a hollow tube using discs to close its ends and having a ring attached to the body to give it a precise weight. However, this is a needlessly complex and expensive way to construct a testing body since the precise weight may be given to a solid testing body when constructed of a plastic material formed by injection molding techniques well known in the art.

In addition, the intraocular pressure of 28.5 gm/cm$^2$ is lower than the generally recognized critical value at which the eye should be given further testing. Studies have shown that 97% of the population have an intraocular pressure of 22 mm Hg or less in healthy eyes and that 65% of known cases of glaucoma have an intraocular pressure of 22 mm Hg or more. By choosing the value of 28.5 gm/cm$^2$, Heine will have a larger number of patients with false positive readings who must be tested further. The value of a screening device such as this, lies in its ability to detect quickly, simply and accurately the small percentage of people with dangerous intraocular pressure. By setting the screening value too low, the accuracy of a device in detecting glaucoma is compromised.

The magnifying lens used by Heine requires that the viewing of a patient's eyes be done from directly overhead. In screening a great number of patients which this invention is designed to do, such a position can be extremely tiring to the person performing the screening. This may result in reduced efficiency of examination and an attendent increase in false readings.

Further, Heine's illuminating means are located above the piston and within the line of sight from the magnifying lens to the weighted body, thereby disturbing the line of clear vision to the applaned area. Since the lighting is provided from above to the top surface of the testing body, there is also the problem of reflection from that surface and a limitation on the accuracy with which the lower surface area can be viewed.

It is apparent that this and other devices are not fully suited to the purpose of providing an inexpensive, easily operated, accurate device for screening the level of intraocular pressure.

SUMMARY OF THE INVENTION

According to the invention, the level of intraocular pressure is determined by resting a piston of precisely determined weight on the cornea of a human eye and comparing the area flattened or applaned by the piston with the area of a circle adjacent to the lower end surface of the piston in contact with the cornea. The piston is made of a transparent material, thereby enabling one to view the area it applanes by viewing through the upper end surface of the piston. The applaned area is compared directly with the area defined by the circle. The lower surface of the piston is optically flat to accurately transmit a view of the applaned area.

A holding means for the piston is made from a transparent material and is designed to have a light source fit on one side. The holder has a circular guide opening in which the piston rides. This guide opening is of a diameter such that the piston rides freely within the guide to eliminate friction which would otherwise prevent the full weight of the piston from resting on the cornea. The holder is further constructed so that the light enters at an angle which will permit maximum internal reflection. The length of the holder between the light source and the piston guide opening is coordinated with the angle at which the light enters so that the maximum amount of light is concentrated around the piston guide.

To further increase the light in this area, a series of roof reflector grooves are formed in the upper surface of the holder surrounding the piston guide opening. These roof reflectors serve to gather and redirect light from the interior of the holder. Further, they are constructed so that they direct light downwardly out of the holder and parallel to the piston.

To concentrate the light received by the piston on its flat lower end surface, a flange projects from the piston. This flange gathers the light reflected from the roof reflectors.

The area applaned by the piston is compared with the area of the indicating circle. If an area equal to or smaller than the circle is applaned, the intraocular pressure is greater than a predetermined value and the patient is then tested for eye diseases. If the area applaned is larger than the inscribed circle, the intraocular pressure is less than the predetermined amount and the probability is that the patient has no eye illness such as glaucoma.

Magnification of the area applaned by the piston may be provided either by use of a convex upper end surface on the piston and/or by positioning a magnifying lens in the line of sight from the eye being tested to the eye of the screening doctor. Magnification is useful so that the examiner may view the area of contact from a greater distance from the eye. In a procedure where a great number of patients must be examined, magnification is of great assistance.

Since the piston must rest freely on the cornea of an eye in order to provide accurate readings, the person examining the eye must be directly above the piston in order to properly view the area of contact where the magnification is vertically aligned with the piston. In examining a number of people, it is more convenient and much less tiring physically for the examiner to view the area of contact from other positions. To accomplish this, a mirror surface is provided for reflecting the view transmitted through the piston. The mirror is positioned above the upper piston surface such that there is an area free of optical obstructions between the upper surface and the mirror. The mirror may be set at a fixed angle or mounted in a support means which allows adjustment of the angle about a horizontal axis. The mirror surface is also rotatable about a vertical axis so that the examiner may be located at various positions beside the patient being examined.

Thus, it can be seen that this device provides a method of screening the level of intraocular pressure which takes only a short time and can be performed by anyone with a minimal amount of training. By providing such a screening device, people can be examined more frequently and in less time than with prior devices. Observations are more simple and accurate, thereby increasing the changes of detecting an eye illness at an early stage.

BRIEF DESCRIPTION OF THE DRAWINGS

FIG. 1 is an exploded view of the tonometer of this invention.

FIG. 2 is a fragmental sectional view of the piston mounted in the holder.

FIG. 3 is a sectional view of the holder taken along line 3—3 of FIG. 1.

FIG. 4 is a diagramatic view of the holder illustrating the line of movement of light.

FIG. 5 is an enlarged elevational view of the piston.

FIG. 6 is a sectional view of the holder and and extension taken along line 6—6 of FIG. 1.

FIG. 7 is an exploded view of an alternative embodiment of the tonometer of this invention.

FIG. 8 is a sectional view of the holder and piston taken along line 8—8 of FIG. 6.

FIG. 9 is an oblique view of the holder of FIG. 6.

DESCRIPTION OF PREFERRED EMBODIMENTS

Referring to FIG. 1, the tonometer includes a piston 10 which is preferably made of a transparent material such as an acrylic resin. Other transparent materials may also be used provided they possess the necessary physical properties such as insolubility, nonporousness, nontoxicity, etc. The shape of the piston 10 is basically cylindrical with a central axis 11 through the longitudinal direction.

The lower end surface 12 of the piston is formed as a circular flat surface which is perpendicular to the central axis. The upper end surface 14 may be flat or alternatively, convex to provide magnification of the lower end surface. Since the piston is preferably constructed by injection molding techniques of acrylic, it is normally a solid body.

According to the invention, piston 10 is required to have a precisely determined weight. When the piston is lowered onto an eye being tested, the weight of the piston applanes an area of the cornea. The area of the cornea which is applaned is a factor both of the internal pressure of the eye and the weight of the piston. If the weight of the piston is too great, it will produce excess internal pressure, thus giving a false reading of the intraocular pressure. It has been found that a weight of 2.2 grams will provide a reading without causing any significant deviation from the true intraocular pressure. Therefore, 2.2 grams is chosen as the preferred piston weight for use in this tonometer. Further, it has been found that the intraocular pressure most useful in screening persons for glaucoma is 22 mm of Hg. At this pressure, a weight of 2.2 grams applanes or flattens an area with a radius of 1.53 mm. Therefore, a circular indicating area 16 which is coaxial with the central axis and shown illustratively as a groove in lower surface 12, has a radius of 1.53 mm.

A holder 18 is provided to support the piston above the eye and guide it into contact with the eye. The holder is preferably constructed to the same transparent material as the piston which can be easily formed by known techniques. A light source 20 may be connected to the holder by means of a piece of rubber tubing 22 to form a socket. As an alternative, the light may be fit into a rigid socket adapted to receive the source 20 at a specific position. In either case, the angle of inclination between the light source and the horizontal base 27 of the holder is designed to be such that it is approximately the natural angular position of the hand of the operator. For example, the tonometer may be manually supported entirely by one hand of the operator which grasps the housing around the light source. The proper angle minimizes physical effort and has been found to be about 30°. The holder 18 provides suport for the piston and includes a guide opening 24 circumscribing the piston 10. Roof reflector surface indicated generally at 25 includes grooves 26 best seen in FIG. 3, which are designed to assist in directing the light from source 20 downwardly out of the holder toward the eye to be tested. The light provided by source 20 enters at the 30° angle above the horizontal base 27 of the holder and, as indicated by the dotted lines in FIG. 4, strikes the base 27 and is reflected at the same angle. A substantial portion of the reflected light is directed to the roof reflector surface 25. The roof reflector surface is of an angle such that light striking it is reflected downward and out of the base surface 27 of the holder 18; in this case, surface 25 is at an angle of 30° from surface 27. The upper surface of grooves 26 define an angle of 90° and thereby provide a two-sided reflection downward, the grooves themselves assist in reflecting the impinging light rather than transmitting the same outward and upward.

When the piston is in place in guide opening 24, the light directed downwardly by the roof reflector surface impinges upon the sloping top surface 28 of flange 29 projecting radially of the piston 10. The flange 29 preferably has an upper frusto-conical surface 28 diverging downwardly toward the lower end surface 12. This surface 28 serves to collect light reflected by the roof reflector surface 25 and to redirect this light from a path substantially parallel to the axis 11 inward to illuminate the lower end surface 12. As will be demonstrated hereafter, the angle of the frusto-conical surface is such that it will direct the light toward the lower end surface 12 and the angle is related to the distance between the frusto-conical surface and the lower end surface such that there is a focusing of the light at the applaned area of the eye.

The flange 29 thereby serves the very important function of concentrating illumination on the lower end surface thus, permitting more accurate viewing of the area of contact with the eye. Since the circular indicating area 16 has a radius of only 1.53 mm, it is apparent that the ease of viewing and the detail with which the circular indicating area 16 may be viewed in critical in judging whether the area applaned by the piston is less than or greaer than the circular indicating area 16. The more light which can be provided to the contact area, the more clearly visible the demarcation line between the area of contact by the lower end surface with the eye will be.

To further aid in screening patients, a mirror surface 30 and a magnifying lens 32 may be provided and supported by an extension 33 of the holder 18. As shown, the extension 33 may be attached to the holder when the mirror and/or magnifying lens is required. As is more clearly shown in FIG. 6, grooves 34 formed on each side of holder 18 receive projections 35 on the lower ends of spring loaded levers 36 to thereby releasably connect the holder 18 and its extension 33. This extension may be constructed of any material either transparent or opaque since it does not have a requirement for light transmission. Alternatively, the holder may be integral with the extension 33.

An upper guide ring 37 on the extension assists in aligning the mirror 30 vertically with the axis of opening 24. The mirror 30, as shown, is a small button with an angled lower surface which is coated to form a mirror surface. When inserted in the ring 37, the mirror surface reflects the view available through the upper end surface 14 of the piston. Mirror 30 is rotatable about a vertical axis so that viewing may take place from various positions surrounding the holder.

Magnifying lens 32 is supported by extension 33 and may be used in conjunction with the mirror 30 in order to enlarge the view presented and provide eye relief to the operator. For ease of aligning the magnifying lens 32 with the mirror (where they are not rigidly connected together) a small pair of indicating marks 38 and 39 may be placed on the mounting which are aligned for proper reflection with minimum distortion.

In operation, a person using this tonometer will grasp the light housing and lower the piston into contact with a patient's eye. When contact is achieved and the piston freely resting on the eye, a view of the contact area is transmitted through the piston to the mirror and by viewing through the magnifying lens 32 an enlarged view of the contact area may be inspected. The person using the instrument in this manner is able to do so by sitting adjacent to the patient whose head would be in a reclining position, either by having the patient lie down or by tilting his head back so that the piston would be perpendicular to the eye with the weight of the piston resting thereon. For viewing from directly above the eye, the person screening a patient may use holder 18 without extension 33. The area of contact is then directly viewed through the upper end surface 14 of the piston 10. However, since viewing from its position must take place at relatively close proximity, it is preferable to use extension 33 and either view the applaned area as described above without additional magnification or place a magnifying lens in the area adapted for holding the mirror 30.

In FIG. 2, a fragmental sectional view of holder 18 and piston 10 are shown. The guide opening 24 is of a diameter greater than the diameter of the upper shaft of the piston 10 so that the piston may freely move up and down in the guide opening 24. As the piston travels downward means, such as an O-ring 40 mounted on the piston prevents it from passing completely through the guide opening 24. Free movement of the piston is essential in placing its full weight on the eye. Any contact with the guide opening may either prevent the full weight from resting on the eye or increase the weight applied thereby giving an inaccurate reading.

Referring now to FIG. 4, light enters the holder 18 perpendicularly through planar surface 41 of light entry guide 42 and moves in a straight line to surface 27. To reflect a major portion of the light, surface 27 should be polished. In the preferred embodiment, the light entry guide is positioned so that light enters at an angle of 30° above the plane of the lower surface 27. Upon striking the lower interior surface, it is substantially reflected at an angle of 30° above the plane of the lower surface toward the roof reflector surface 25. The roof reflector surface 25 is at an angle of 30° above the lower surface 27 and upon striking this surface, a large portion of the light is thereby directed downward so that it exits through the lower surface of holder 18 approximately perpendicular to the lower surface. While other configurations are possible, it is apparent that a change in the angle of entry of light would necessitate a change in the dimensions of the holder. For example, an increase in the angle at which light enters with respect to surface 27 would require the height or the width of the holder to be decreased (or both) so that the light reflected by the lower interior surface of the holder would reach the roof reflector.

By way of example, it is desired to provide a piston of acrylic resin weighing 2.2 grams. Such a piston 10 is shown in FIG. 5 wherein the shaft extends a distance A from the upper end surface 14 to the top of the frusto-conical surface. The axial length of the frusto-conical surface 28 is B and the axis length of the cylindrical portion of flange 29 is C. The axial length from the flange to the lower end surface 12 is D. The angle of the frusto-conical surface below a horizontal line is depicted as E. The diameter of the upper shaft of the piston is F and the diameters of the piston immediately below the flange and at the lower end surface are G and H respectively. In a preferred embodiment, the distances in inches and angles used for construction of the piston were as follows: A = 1.000; B = 0.063; C = 0.064; D = 0.310; E = 39°; F = 0.300; G = 0.374; and H = 0.260.

Referring now to FIGS. 7 and 8, showing an alternative construction for a tonometer, the piston 43 is again constructed of a transparent material. It has a lower end surface 44 and an upper end surface 45, both of which are shown as perpendicular to the central axis 46. Alternatively, the upper end surface 45 may be convex to provide magnification of the view through the piston. A circumferential notch 47 is formed in the piston. This notch is primarily used as an indicating means for reasons to be explained subsequently.

Light from a source (not shown) enters the holder 48 through an entry guide or socket 50 opening to a cylindrical conduit 52 extending to guide opening 54.

In using this tonometer, the observer should position the holder such that the maximum amount of light is directed to the area applaned by the piston. To do so, the holder 48 is raised or lowered until the notch 47 is aligned with conduit 52. At this point light is partially transmitted downward into the piston to illuminate the applaned area and partially reflected to the upper surface of the notch which reflects the same radially. Thus, the notch serves to indicate the proper positioning of the holder and also serves as a safety feature. If the operator lowers the holder below this point, the holder might contact and injure the eye; the radial light reflection from the upper surface of the notch will cease when the conduit 52 gets below the notch and this warns the operator to lower no further. obviously, the length of the piston below the notch must be greater than the height of the inner end of the conduit from the lower surface of the holder.

Indicating circle 58 on the lower end of the piston, shown as being adjacent to the lower end surface 44 and coaxial with central axis 46, provides a means for determining the size of the applaned area. The diameter of circle 58 and the weight of piston 43, are identical with those of piston 10 of FIG. 1.

Although it is not shown in FIG. 7, an extension of holder 48 may be constructed similar to extension 33 in FIG. 1, whereby a mirror surface and magnifying means may be supported for ease of viewing the applaned area. However, a shoulder 60 in the guide opening of the holder and flange 62 on the piston are substituted for the O-ring 40 in the prior embodiment.

Having thus described the invention in its preferred embodiments, it will be clear to those having ordinary skill in the art that various modifications may be made in the apparatus without departing from the spirit of the invention. It is not intended that the invention be limited by the illustrated embodiments nor the language used to describe them, rather, it is intended that the invention be limited only by the appended claims.

I claim:

1. An applanation tonometer including a transparent piston having a central axis extending from a flat, lower-end surface adapted to rest on the eye of a patient to an upper-end surface, a source of light and holder means for supporting said piston above the eye and guiding it into contact with the eye so that an area of the eye may be applaned by the lower-end surface of the piston;

conduit means in said holder means for conducting light from said source to the surface of said piston, notch means in the surface of said piston for (1) receiving and transmitting a portion of said light downward within the piston to its lower end surface and (2) reflecting another portion of said light radially of said piston.

2. The tonometer of claim 1, wherein the piston has a circular lower end surface coaxial with said central axis and includes means for showing a circle located coaxial with said central axis as viewed from the upper end surface.

3. The tonometer of claim 2, including means remote from the lower end surface for magnifying the lower end surface and the circle.

4. The tonometer of claim 1, wherein the said piston has a mass of 2.2 grams and the said circle has a radius of 1.53 mm.

5. An applanation tonometer including: a source of light; a transparent piston having a central axis extending from an upper-end surface to a flat, circular, lower-end surface coaxial with the central axis and adapted to rest on the eye of a patient, wherein the lower-end surface includes means for showing a circle located coaxial with the central axis as viewed from the upper-end surface; and, transparent holder means for supporting the piston above the eye and guiding it into contact with the eye so that an area of the eye may be applaned by the lower-end surface, wherein the holder means includes light reflecting surface means adapted to direct a portion of the light entering the holder from the source so that it exits the holder externally of the piston and extends downwardly toward the lower-end surface of the piston and parallel to the central axis; with said piston having a transparent, frusto-conical flange means sloping downwardly in the direction of the lower-end surface and extending radially of the central axis, said flange means adapted to collect said downwardly directed light and concentrate it into the piston and toward the lower-end surface.

6. The tonometer of claim 5, including means remote from the lower-end surface for magnifying the lower-end surface and the circle.

7. The tonometer of claim 5, including a mirror mounted on the holder remote from the upper piston surface, the space between said upper surface and said mirror being free of optical obstructions whereby a view of the eye contact area is transmitted to the mirror, said mirror being adjustable on its mounting to modify the angle of reflection of the image transmitted from the upper piston surface.

8. The tonometer of claim 5, wherein the said piston has a mass of 2.2 grams and the said circle has radius of 1.53 mm.

* * * * *